(12) United States Patent
Chitre

(10) Patent No.: US 7,123,969 B1
(45) Date of Patent: Oct. 17, 2006

(54) LEAD HAVING ONE OR MORE LOW POLARIZATION ELECTRODES

(75) Inventor: Yougandh Chitre, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 485 days.

(21) Appl. No.: 10/443,240

(22) Filed: May 21, 2003

(51) Int. Cl.
A61N 1/00 (2006.01)

(52) U.S. Cl. ..................................... 607/121; 607/122

(58) Field of Classification Search ........ 600/372–374; 607/115, 116, 119, 122, 129, 121
See application file for complete search history.

(56) References Cited

U.S. PATENT DOCUMENTS

| | | | | |
|---|---|---|---|---|
| 2,960,642 A | * | 11/1960 | De Rudnay | 361/322 |
| 3,292,062 A | * | 12/1966 | Gallagher et al. | 361/321.5 |
| 4,628,933 A | * | 12/1986 | Michelson | 607/53 |
| 4,679,572 A | | 7/1987 | Baker, Jr. | 128/786 |
| 5,318,572 A | | 6/1994 | Helland et al. | 607/121 |
| 5,628,778 A | | 5/1997 | Kruse et al. | 607/123 |
| 5,645,580 A | | 7/1997 | Moaddeb et al. | 607/122 |
| 5,851,896 A | | 12/1998 | Summerfelt | 438/396 |
| 5,935,158 A | | 8/1999 | Holmstrom et al. | 607/116 |
| 5,964,794 A | * | 10/1999 | Bolz et al. | 607/121 |
| 5,995,876 A | | 11/1999 | Kruse et al. | 607/123 |
| 6,240,320 B1 | | 5/2001 | Spehr et al. | 607/122 |
| 6,253,110 B1 | | 6/2001 | Brabec et al. | 607/116 |
| 6,292,704 B1 | | 9/2001 | Malonek et al. | 607/121 |
| 6,339,723 B1 | | 1/2002 | Sloman | 607/28 |
| 2003/0220677 A1 | * | 11/2003 | Doan et al. | 607/122 |
| 2004/0176828 A1 | * | 9/2004 | O'Brien | 607/119 |
| 2005/0075709 A1 | * | 4/2005 | Brennen et al. | 607/122 |

* cited by examiner

Primary Examiner—Mark Bockelman

(57) ABSTRACT

A low-polarization electrode for use with an implantable lead. The low polarization electrode comprises a base substrate of a conductive material, an intermediate layer of a high dielectric layer over the base substrate, and a polarization-reducing coating over the intermediate layer. The low-polarization electrode essentially operates as a parallel-plate capacitor, thereby alleviating the polarization artifact at an electrode/tissue interface.

17 Claims, 2 Drawing Sheets

LEAD HAVING ONE OR MORE LOW POLARIZATION ELECTRODES

FIELD OF THE INVENTION

The present invention generally relates to leads for connecting implantable medical devices with selected body tissue. More particularly, the invention relates to a low-polarization electrode for use with such leads.

BACKGROUND

As is well known, pacemakers are implanted in patients to deliver electrical stimulation pulses to the patient's heart via one or more electrodes mounted on one or more leads. In addition to being used to stimulate the patient's heart, the electrodes are also frequently used to sense electrical activity of the heart, often in response to the stimulation pulses. It would be desirable to use the same electrode both for stimulating the patient's heart and for sensing corresponding heart activity. However, delivering a stimulation pulse through an electrode results in what is referred to as lead polarization. Lead polarization is a post-stimulation artifact that results from an accumulation of charge at the electrode/tissue interface following an electrical stimulation pulse. This lead polarization (or "after-potential") can hinder or even prevent the accurate sensing of intrinsic cardiac electrical activity that follows soon after the stimulation pulse (e.g., the evoked response of the heart tissue caused by the stimulation pulse). In some instances, the electrode or electrodes used to deliver the stimulation pulses are not able to discriminate between the after-potential and an evoked response signal, and therefore other electrodes must be used to detect cardiac activity. This requires the provision of additional electrodes that are relatively far from the site of interest, which is disadvantageous, and also requires a lead with additional components.

In modern pacing leads the electrodes, both of the tip and ring variety, often employ a surface coating of titanium nitride (TiN). The implementation of TiN as a coating material was an improvement in the pacing industry by providing an electrode/tissue interface with increased electrode/tissue capacitance. The increase in interface capacitance is a result of the increased active surface area brought about by the fractal morphology of the sputter-coated titanium nitride material. The increase in interface capacitance, in turn, lowers the polarization artifact typically seen following the pacing pulse. This falls out from the equation describing the after-potential or polarization given by equation (1), as follows.

$$U_C(t > T) = U_r \left(1 - \exp\left(\frac{-T}{R_L C_H}\right)\right) \exp\left(\frac{-(t-T)}{R_L C_H}\right) \quad (1)$$

where:
$R_L$: resistance of the lead
$C_H$: Helmholtz capacitance
$U_r$: charge voltage
$U_c$: polarization value Although the lowering of the polarization value can be achieved by increasing the lead length, which in turn increases $R_L$ (the resistance of the lead), it compromises the sensing functionality of the electrode and increases energy consumption. See Schaldach, "The Electrode-Electrolyte Interface", *Electrotherapy of the Heart*, Spr-Vlg, 1992.

General disclosures of body implantable electrode constructions in which either or both of the leads and electrodes are constructed of titanium or titanium alloys are well known. Other implantable medical devices are known that include a pulse generator and associated electrodes designed to prevent leakage currents in the output circuit. This is accomplished by utilization of the electrode lead-to-tissue electrolytic interface capacitance (Helmholtz capacitance) with a highly leakage resistant layer interfaced together with and formed, for example, by titanium and titanium dioxide. Moreover, electrodes for muscle stimulation are known which feature a platinum electrode which has preferably been platinized to develop a coating of platinum black, contained in a second electrode housing of suitable electrode metal which is compatible with platinum such as titanium. Finally, the use of a platinum black coating with materials other than titanium are also known to reduce source impedance and polarization. Indeed, the use of a platinum black coating with titanium has long been known to reduce source impedance and polarization.

While advances have been made in the construction of leads that provide lower polarization values, there is still a need for leads that provide even lower polarization artifacts, particularly in the case of electrodes to be used to perform both pacing and sensing.

SUMMARY

What is disclosed herein is an implantable lead for stimulating a heart that includes one or more electrodes that exhibit relatively low polarization values. The implantable lead includes one or more stimulating electrodes (e.g., a cathode electrode) that may directly contact heart tissue. The electrode is designed to provide low polarization values, which results in the electrode being suitable for use as both a pacing electrode and a sensing electrode. The lead further includes a suitable conductor connected to the electrode to provide stimulation energy to the electrode and to transmit electrical signals sensed by the electrode. The cathode electrode is comprised of a base substrate, an intermediate layer of a highly dielectric material, and a polarization reducing coating that is applied over the base substrate.

Other and further features, advantages, and benefits of the invention will become apparent in the following description taken in conjunction with the following drawings. It is to be understood that the foregoing general description and the following detailed description are exemplary and explanatory but are not to be restrictive. The accompanying drawings which are incorporated in and constitute a part of this invention, illustrate one of the embodiments of the invention, and together with the description, serve to explain the principles of the invention in general terms. Like numerals refer to like parts throughout the disclosure.

BRIEF DESCRIPTION OF THE DRAWINGS

The foregoing aspects and other features of the present invention are explained in the following description, taken in connection with the accompanying drawings, wherein.

DETAILED DESCRIPTION

Figure 1:
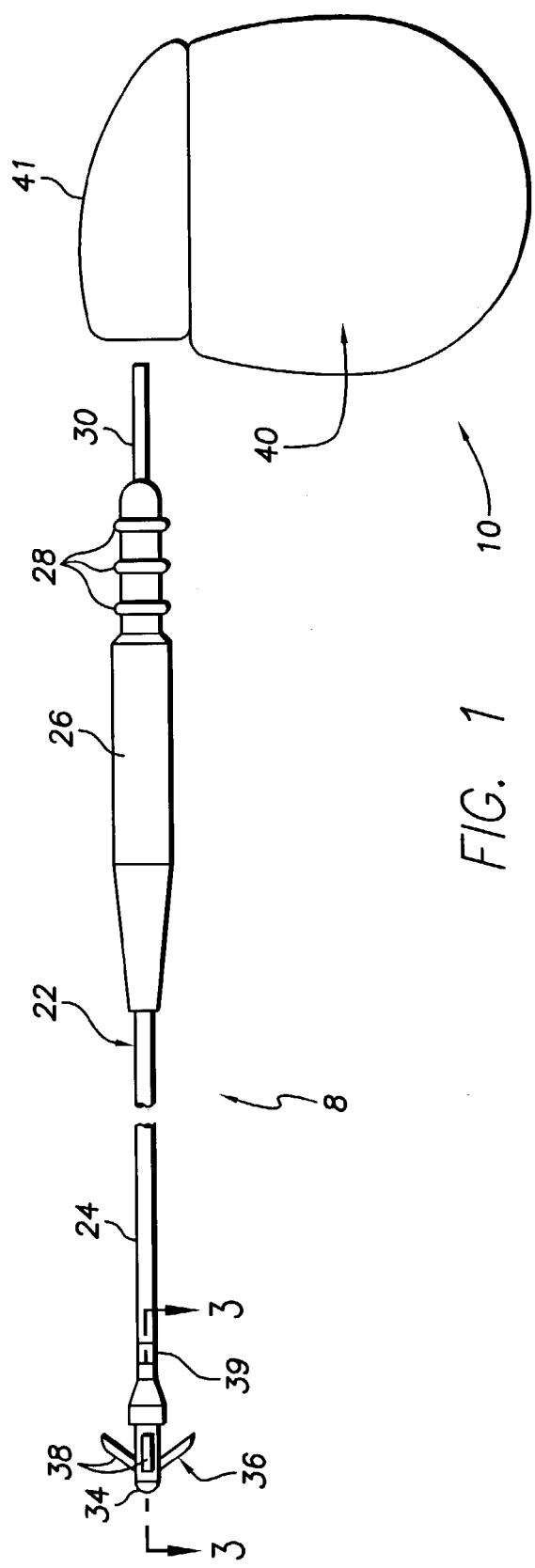
FIG. 1 is a side elevation view of an implantable cardiac stimulating system according to one embodiment.

Referring now to FIG. 1, there is shown a side view of a tissue stimulating system 8 including one or more electrodes 34 and/or 39 constructed according to a preferred embodiment. Although the system 8 will be described with reference to the embodiment shown in the drawings, it should be understood that the one or more electrodes 34 and/or 39 may be used in connection with various embodiments of tissue stimulating systems.

The tissue stimulation system 8 includes a conventional implantable stimulation device 10. As is well known, stimulation device 10 interacts with a patient's heart (not shown) by way of one or more leads, such as lead 22. Lead 22 is suitable for delivering stimulation to a patient's heart via electrodes 34 and 39, and furthermore is capable of sensing electrical activity within the heart via electrodes 34 and 39, and delivering corresponding electrical signals to stimulation device 10 for processing. While only a single lead 22 is shown in FIG. 1, it is well known to those skilled in the art that stimulation device 10 may be connected to multiple leads to provide multi-chamber stimulation and/or sensing.

As is well known in the art, implantable stimulation device 10 is capable of treating fast and/or slow arrhythmias with stimulation therapy, including cardioversion, defibrillation, and/or pacing stimulation. A more detailed description of an implantable stimulation device with which the lead 22 may be utilized is found in U.S. Pat. No. 6,339,723, which is expressly incorporated herein by reference.

Implantable stimulation device 10 includes a housing 40 and a connector (or header) 41 connected to housing 40 and having a plurality of terminals (not shown) that provide electrical connections with the respective electrodes of lead 22, as is well known to those skilled in the art.

Referring to FIG. 1, lead 22 is preferably covered with an insulation sheath 24 fabricated of silicone rubber, polyurethane, or other suitable insulative material. A connector assembly 26 located at the proximal end of the lead 22 is provided with one or more sealing rings 28 and carries one or more connector pins 30 for connection in a known manner with housing connector 41 to provide electrical stimulation energy to the electrodes of the lead 22. Connector pin 30 may be fabricated of stainless steel or other electrically conductive material to establish electrical conduction between device 10 and one or more of electrodes 34 and 39.

Figure 2:
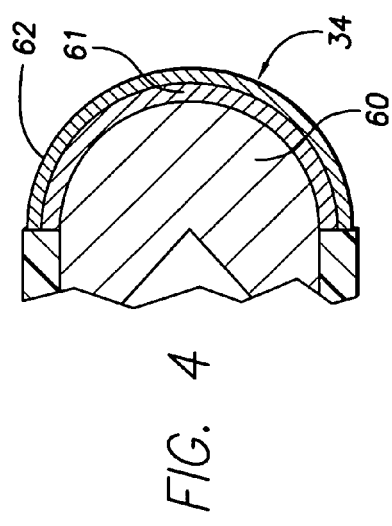
FIG. 2 is an enlarged view of a distal region of a lead in accordance with one exemplary embodiment.

At the distal end of lead 22 is electrode 34 (i.e., tip electrode) and, in one embodiment, adjacent to electrode 34 is an anchor assembly 36 that carries a plurality of circumferentially spaced tines 38 (FIGS. 1 and 2). The tines 38 engage heart tissue and urge electrode 34 into contact with the endocardial tissue. It will be apparent to those skilled in the art that other suitable fixation devices may be used, including active and passive fixation devices.

In one embodiment, electrode 39 is connected to lead 22 and is spaced from the first electrode 34 a predetermined distance so as to provide bipolar pacing and/or sensing in conjunction with electrode 34 (FIGS. 1 and 2). In the disclosed embodiment, electrode 39 is in the form of a ring electrode, although it will be understood that electrode 39 may take other forms as well.

Figure 3:
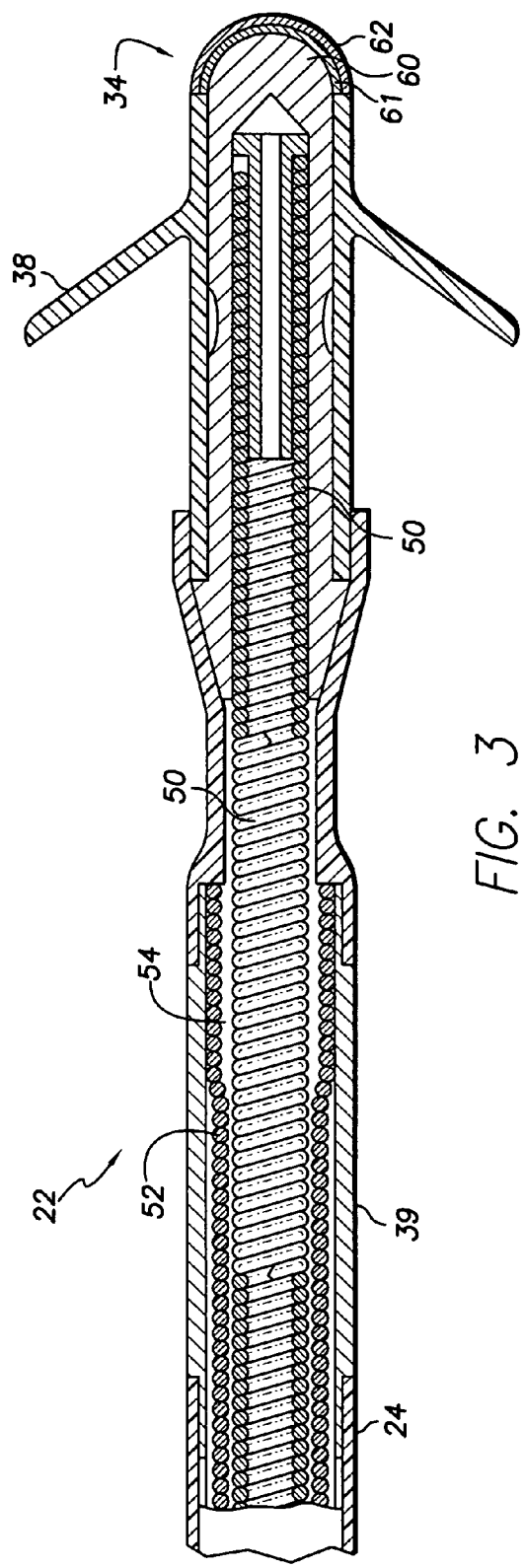
FIG. 3 is a cross-sectional view taken along line 3—3 of FIG. 1.

In one embodiment, lead 22 includes a pair of coiled, coaxial conductors 50 and 52 (FIG. 3) that are electrically connected to the respective electrodes 34 and 39 (FIG. 3). Coils 50 and 52 are electrically isolated from each other by a tubular insulating layer 54 disposed between the coils. Alternatively, each coiled conductor can be individually insulated to maintain electrical isolation between the respective conductors. The conductors extend through the lead body and are electrically connected to sensing and/or pulse generating circuitry within the implantable cardiac device 10 via the connector assembly 26, as described above and as is well known in the art.

As shown in FIG. 3, outer conductor 52 establishes electrical communication with electrode 39, while inner conductor 50 establishes electrical communication with electrode 34.

In another embodiment, one or both of the conductors 50 and 52 may be in the form of cable or wire conductors. Again, electrical isolation may be achieved in various manners, as described above. Alternatively, both conductors may be in the form of cable or wire conductors.

In one embodiment, distal electrode 34 serves as the cathodal electrode, while the second electrode 39 serves as the anodal electrode for bipolar pacing and/or sensing.

Figure 4:
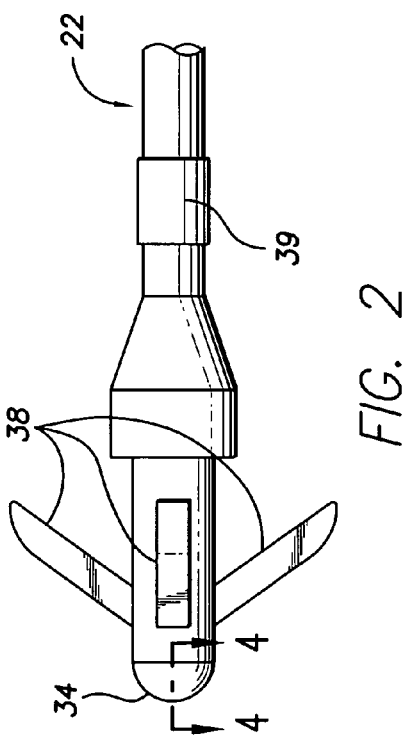
FIG. 4 is a cross-sectional view taken along line 4—4 of FIG. 2.

Preferably, distal electrode 34 is formed of a multilayer construction. Referring to FIGS. 3 and 4, distal electrode 34 includes a base substrate 60, an intermediate layer 61 formed of a dielectric material, and a polarization-reducing outer layer 62 over intermediate layer 61.

The base substrate 60 is formed of a conductive, inert material, and preferably of platinum iridium. In one embodiment, base substrate 60 is formed of one or more members of the platinum group (also known as "platinum metals", or the platinum-like metals in Group VIII of the Periodic Table of Elements), namely ruthenium, rhodium, palladium, osmium, iridium, platinum, as well as any combination thereof (e.g., an alloy of two or more of the listed metals). Alternatively, the base substrate 60 may be formed of titanium or any other suitable inert metal.

In one embodiment, the intermediate layer 61 is formed of a material that exhibits a high dielectric constant. In one illustrative embodiment, the material comprises barium titanate. The thickness of intermediate layer 61 is preferably about 3 microns or greater, although smaller or larger thicknesses may also be used. Preferably, the material used for intermediate layer 61 has a dielectric constant (K) of at least about 10, although materials having other dielectric constants may also be used.

By providing the intermediate layer 61 having a high dielectric constant, the electrode essentially operates as a parallel-plate capacitor, thereby alleviating the polarization artifact at the electrode/tissue interface. Inclusion of intermediate layer 61 therefore serves to remove at least a portion of the charge from the electrode/tissue interface.

Polarization-reducing outer layer 62 provides a fractal surface structure and relatively large surface area, which increases the capacitance at the interface between layers 61 and 62 and serves to further reduce the polarization artifact at the electrode/tissue interface. In one illustrative embodiment, outer layer 62 is formed of titanium nitride, although other porous structures may also be used, such as iridium oxide, platinum black, and the like. In one illustrative embodiment, the thickness of outer layer 62 is between about 3 and about 12 microns, although other thicknesses may be used.

In a bipolar configuration, ring electrode 39 can be formed having the same three layers 60, 61, and 62 as tip electrode 34, or may be any conventional electrode. In addition, in a unipolar configuration (i.e., with the housing 40 used as the return electrode) the three-layer electrode described hereinabove may be either the tip electrode or a proximal electrode.

Thus, the novel electrode design described herein may be used in various configurations. By way of example, the electrode can be used in a bipolar configuration with a conventional electrode, in a bipolar configuration with an identical electrode, in a unipolar configuration where the novel electrode is the tip electrode, or in a unipolar configuration where the novel electrode is proximal to the distal tip of lead 22.

Because the novel electrode disclosed herein provides relatively low polarization artifacts, the electrode is suitable both for stimulating heart tissue and for sensing cardiac activity following the delivery of stimulation energy to the heart tissue. For example, in a bipolar configuration, the tip electrode 34 preferably is formed with the novel three-layer construction described herein, because that electrode will contact heart tissue and will therefore define an electrode/tissue interface. The proximal electrode 39 may be either a conventional electrode or formed having the same three-layer construction as electrode 34. Stimulation pulses may be delivered between electrodes 34 and 39, and subsequent cardiac activity may be sensed between those same electrodes, or between electrode 34 and a different electrode.

It should be understood that the foregoing description is only illustrative of various embodiments. Various alternatives and modifications can be devised by those skilled in the art. For example, while lead 22 is shown in FIGS. 1–3 as including the pair of electrodes 34 and 39, it will be apparent to those skilled in the art that the novel electrode disclosed herein is suitable for use in connection with leads having a single electrode, or with leads having more than two electrodes. Accordingly, the present invention is intended to embrace all such alternatives, modifications and variances that fall within the scope of the appended claims.

What is claimed is:

1. An implantable lead for use with an implantable cardiac stimulation device, the lead comprising:
   a lead body;
   a cathode electrode connected to the lead body, the cathode electrode comprising a base substrate of a conductive material, the cathode electrode further comprising an intermediate layer of an inorganic high dielectric material, and the cathode electrode further comprising a polarization-reducing inorganic coating over the intermediate layer, the polarization-reducing coating adapted to be in direct contact with heart tissue; and
   a second electrode connected to the lead body and displaced from the cathode electrode.

2. The lead of claim 1, wherein the polarization-reducing coating comprises titanium nitride.

3. The lead of claim 1 wherein the intermediate layer comprises barium titanate.

4. The lead of claim 1, wherein the second electrode comprises an anodal electrode.

5. The lead of claim 1, further comprising a pair of conductors extending within the lead, the conductors being electrically coupled to the respective cathode and second electrodes.

6. The lead of claim 1, wherein the base substrate is formed of an alloy of platinum and iridium.

7. The lead of claim 1, wherein the cathode electrode comprises a tip electrode disposed at a distal end of the lead body, and wherein the second electrode is spaced a selected distance from the distal end of the lead body.

8. The lead of claim 1, wherein the intermediate layer has a dielectric constant of at least about 10.

9. The lead of claim 1 wherein the intermediate layer is 2 microns or greater and has a dielectric constant of at least about 10.

10. An implantable cardiac system comprising:
    an implantable cardiac stimulation device configured for implant within a patient and that is operative to perform at least one of pacing, sensing, cardioversion, and defibrillation;
    a lead body configured for implant within the patient and for connection to the implantable cardiac stimulation device;
    a cathode electrode connected to the lead body, the cathode electrode comprising a base substrate of a conductive material, the cathode electrode further comprising an intermediate layer of an inorganic high dielectric material, and the cathode electrode further comprising a polarization-reducing inorganic coating over the intermediate layer, the polarization-reducing coating adapted to be in direct contact with heart tissue; and
    a second electrode connected to the lead body and displaced from the cathode electrode.

11. The implantable cardiac system of claim 10, wherein the polarization-reducing coating comprises titanium nitride.

12. The implantable cardiac system of claim 10 wherein the intermediate layer comprises barium titanate.

13. The implantable cardiac system of claim 10, wherein the first electrode comprises a cathodal electrode and the second electrode comprises an anodal electrode.

14. The implantable cardiac system of claim 10, further comprising a pair of conductors extending within the lead, the conductors being electrically coupled to the respective cathode and second electrodes.

15. The implantable cardiac system of claim 10, wherein the base substrate is formed of an alloy of platinum and iridium.

16. The implantable cardiac system of claim 10 wherein the intermediate layer has a dielectric constant of at least about 10.

17. The implantable cardiac system of claim 10, wherein the intermediate layer is 2 microns or greater and has a dielectric constant of at least about 10.

* * * * *